United States Patent [19]

Sato et al.

[11] 4,371,577
[45] Feb. 1, 1983

[54] ANTIMICROBIAL CARPET CONTAINING AMINO ACID TYPE SURFACTANT

[75] Inventors: Minoru Sato, Gifu; Yoshiteru Hirose, Kamakura; Shigeshi Toyoshima, Funabashi, all of Japan

[73] Assignees: Mitsubishi Burlington Co., Ltd.; Ajinomoto Co., Ltd.; Mitsui & Co., Ltd., all of Tokyo, Japan

[21] Appl. No.: 372,139

[22] Filed: Apr. 27, 1982

[30] Foreign Application Priority Data

May 22, 1981 [JP] Japan ................................. 56-76755

[51] Int. Cl.$^3$ .......................... B32B 3/02; B32B 33/00
[52] U.S. Cl. ........................................... 428/96; 139/2; 139/3; 139/7 R; 156/72; 428/97; 428/907
[58] Field of Search ............................ 428/96, 97, 907; 156/72; 139/2, 3, 7 R

[56] References Cited

U.S. PATENT DOCUMENTS 4,313,978 2/1982 Stevens et al. ........................ 428/96
4,343,853 8/1982 Morrison ............................. 428/907

*Primary Examiner*—Marion E. McCamish
*Attorney, Agent, or Firm*—Antonelli, Terry & Wands

[57] ABSTRACT

An antimicrobial carpet having bacteriostatic and sterilizing effect against molds, bacteria and viruses is prepared by incorporating into fibrous materials prior to or after fabrication into a carpet an amino acid type surfactant represented by the formula:

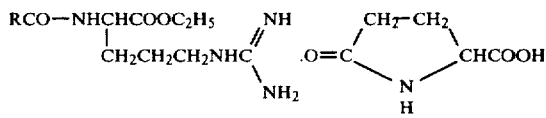

wherein RCO is a $C_8$–$C_{16}$ fatty acid residue.

11 Claims, No Drawings

ANTIMICROBIAL CARPET CONTAINING AMINO ACID TYPE SURFACTANT

BACKGROUND OF THE INVENTION

This invention relates to an antimicrobial carpet very effective for sterilizing molds, bacteria and viruses and a method for preparation thereof.

There exist in the air various molds, bacteria and viruses which affect deleterious influences upon human bodies. Particularly, in medical facilities such as hospitals, pathogens brought about by patients and visitors are floating in the rooms or sedimented on the floors in such facilities, whereby serious influences such as infection of the patients or visitors directly or indirectly with pathogens may be caused. For prevention of such infections in medical facilities, there have been adopted various methods. For example, there may be mentioned such methods as filtration of the air by means of a filter, thorough cleaning or sterilization of the floors, etc.

However, in conventional medical facilities wherein the floors are finished with rigid materials such as plastic tiles, molds, bacteria or viruses as pathogens brought about by patients or visitors will exist attached as such on the dust. Most of these pathogens, even if once sedimented on the floor after floating, will be floated again in the air by movement of passengers or others, thus repeating floating-sedimentation cycles. Consequently, removal efficiency by filtration of the contaminated air by means of a filter is low and also it is impossible to remove the microorganisms to a satisfactory extent by mopping or with the use of a dust collector. While spraying of a sterilizing agent on the floors may give a temporary sterilizing effect, it is difficult to keep the sterilizing effect persistently in a polyclinic hospital wherein there are frequent going in and out of persons. For the reasons mentioned above, it is very difficult to prevent infection within medical facilities to a satisfactory extent.

SUMMARY OF THE INVENTION

The object of the present invention is to provide an antimicrobial carpet having sterilizing effect against molds, bacteria and viruses.

The other object of the present invention is to provide an antimicrobial carpet suitable as floor material for medical facilities which can prevent infection in medical facilities such as hospitals.

In one aspect of the present invention, there is provided an antimicrobial carpet constituted of a fibrous material containing an amino acid type surfactant represented by the formula shown below impregnated therein.

In another aspect of the present invention, there is also provided a method for preparation of an antimicrobial carpet by fabricating a fibrous material into a carpet, wherein the improvement comprises subjecting the fibrous material prior to or after fabrication into a carpet structure to a treatment with an amino acid type surfactant represented by the formula shown below.

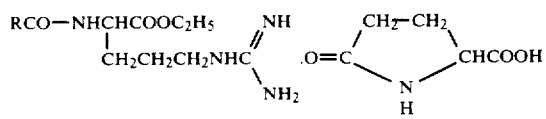

wherein RCO is a $C_8$–$C_{16}$ fatty acid residue, thereby to produce an antimicrobial carpet.

DETAILED DESCRIPTION OF THE INVENTION

The amino acid type surfactant to be used in the present invention has excellent bacteriostatic and sterilizing effects against molds, bacteria and viruses, and can exhibit very excellent effects against microorganisms, including not only molds such as *Aspergillus niger, Penicillum funiculosum, Aspergillus oryzae, Rhizopus nigricans, Trichophyton interdigital*, etc. and bacteria such as *Escherichia coli, Pseudomonas aeruginosa, Proteus vulgaris, Staphylococcus aureus, Bacillus subtilus, Corynebacterium dephtheriae, Candida albicans, Streptococcus faccalis*, etc. but also viruses, especially hepatitis B virus (HB virus).

The amino acid type surfactant to be used in the present invention can be prepared according to the method as disclosed in Japanese patent publication No. 5413/76, namely by condensing L-alginine, a kind of amino acids, with a natural fatty acid such as capric acid, lauric acid, palmitic acid, coconut oil fatty acid, tallow fatty acid, etc. to form an ester, which ester is further neutralized with DL-pyrrolidone carboxylic acid derived from an amino acid into a salt. The amino acid type surfactant, while it exhibits excellent bacteriostatic and sterilizing effects against molds, bacteria, etc., is soluble in water to have a surface active action and at the same time highly safe with respect to acute toxicity ($LD_{50}$), irritation to skin and ophthalmic mucosa. Moreover, it has good biodegradable characteristic and can rapidly be decomposed in wastewaters.

As the carpet to be impregnated with the aforesaid amino acid type surfactant in the present invention, there may be employed those made of fibrous materials, including synthetic fibers such as polyamide fibers, acrylic fibers, polyester fibers, polypropylene fibers, etc.; regenerated fibers such as rayon; and natural fibers such as wool, hemp or others, and having a textile surface of fibers formed by Tufting machine, Wilton loom, Needle punching machine, or Fusion bonding machine.

The antimicrobial carpet according to the present invention can be prepared by the methods which can be classified broadly into the two categories as described below.

According to one method, fibrous materials in any desired form before formation into a carpet such as pile yarns, carpet foundations, or yarns for carpet foundations are subjected to the impregnation treatment with an amino acid type surfactant as described above to have the amino acid type surfactant attached on fibrous materials, followed by fabrication into carpets by any desired means as mentioned above.

The other method comprises subjecting a carpet fabricated from fibrous materials according to any desired method to impregnation treatment with an amino acid type surfactant to have the amino acid type surfactant attached onto fibrous materials.

In the present invention, the amino acid type surfactant may preferably be attached on fibrous materials, especially on the fibrous material located on the surface of a carpet. The amount of an amino acid type surfactant attached may preferably be 0.01 to 5% by weight. To describe the impregnation treatment with an amino acid type surfactant in further detail, an aqueous solution containing 0.01 to 30% by weight of an amino acid type surfactant, which may optionally be added with a water-soluble thermosetting binder or a water-soluble thermoplastic binder or further with another antimicrobial agent, is imparted to carpets or fibrous materials for constituting carpets according to such methods as dipping, spraying, etc., followed by drying at 100° to 150° C., thereby to attach a predetermined amount of an amino acid type surfactant onto fibrous materials.

When an aqueous amino acid type surfactant solution is imparted according to the dipping method, it is preferred to perform the treatment under the conditions of a temperature within the range from 20° to 98° C. for 1 minute to 2 hours.

Particularly, in the present invention, further enhanced effect can be achieved against viruses by attaching in combination with an amino acid type surfactant to the fibrous materials in an amount of 0.01 to 5% by weight an organosilicone quaternary ammonium salt, which is a known antibacterial agent, exhibiting no antiviral effect when used alone, represented by the formula:

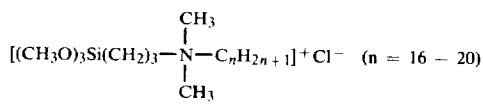

In this case, it is preferred to use an amino acid type surfactant and an organosilicone quaternary ammonium salt at a ratio of 1:5 to 1:0.4 (weight ratio). Further, if necessary, a fluorine type anti-contamination agent may also be permitted to co-exist with these ingredients.

It is also very preferable in the present invention to impart anti-contamination property simultaneously with sterilizing effect to fibrous materials constituting the carpet, since the carpet of the present invention is suitable for use as floor materials in medical facilities. As the method for imparting such an anti-contamination property, a fluorine type anti-contaminating agent may be added to fibrous materials, preferably into an aqueous solution of an amino acid type surfactant at the time of the impregnation treatment of fibrous materials after fabrication into carpets with an amino acid type surfactant or alternatively a fluorine type anti-contaminating agent may be attached by spraying or other methods onto the fibrous materials after the impregnation treatment. There can be obtained a carpet excellent in anti-contaminating property by attaching a fluorine type anti-contaminating agent to the fibrous materials on the carpet surface in an amount of 0.1 to 30% by weight based on the fibrous materials according to the methods as described above. As such a fluorine type anti-contaminating agent, there may be employed organic fluorine compounds such as AG-800 (produced by Asahi Glass CO., Ltd., Japan), Teflon C-19A, C-SF (produced by E. I. Du Pont de Nemours & Co.), Scotch Guard FC-376 (3M Corporation), Dick Guard CP (Dainippon Ink Chemical Co., Ltd., Japan), or other commercial products.

The carpet according to the present invention, through the excellent bacteriostatic and sterilizing effect of an amino acid type surfactant attached on the birous material thereof against molds, bacteria and viruses can not only have sterilizing action on the molds, bacteria and viruses contacted or near the carpet, but also is free from contamination of the carpet per se through proliferation of molds, bacteria, etc. The carpet according to the present invention has a structure with a textile surface and therefore has the so called dust pocket function capable of collecting dust, thereby reducing markedly refloating molds or bacteria by trapping the dust on which molds or bacteria are attached. With such effects, the carpet of the present invention is of course suitable for use as floor material in medical facilities, but it is also useful as floor materials in facilities in other fields such as food hygiene or environmental hygiene.

The present invention is further illustrated by referring to the following Examples.

EXAMPLE 1

A tufted carpet with a pile shape of level loop, a pile length of 5 mm and a pile yarn weight of 1000 g/m² fabricated with the use of bulky yarns of 6,6-nylon as pile yarns and a polypropylene fabric as foundation was dyed with a cation dye, an acidic dye and a disperse dye by means of a winch dyeing machine and thereafter an amino acid type surfactant of the formula:

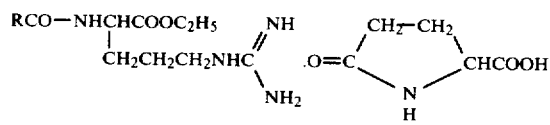

wherein RCO is a coconut oil fatty acid residue, (hereinafter referred to as CAE) as 1.5% by weight and 2.5% by weight aqueous solutions was sprayed on the pile surface of the tufted carpet, followed by drying at 130° C. for 15 minutes to have CAE attached in amounts of 0.3% by weight and 0.5% by weight, respectively.

On a culture medium for sensitive disc, there was coated 0.1 ml of *Staphylococcus aureus* (in ordinary bouillon, cultivated at 37° C. for 24 hours) and the above two kinds of treated carpets and untreated carpet each cut into a strip of about 3 cm square were placed thereon, and about 10 ml of a culture medium for sensitive disc was thinly layered thereon. After cultivation at 37° C. for 24 hours, the width of inhibited zone was measured to give the results as shown in Table 1, which indicates that the present carpet has excellent sterilizing effect.

TABLE 1

| Amount of CAE attached (% by weight) | Width of inhibited zone (mm) |
|---|---|
| 0 | 0 |
| 0.3 | 5.2 |
| 0.5 | 8.5 |

EXAMPLE 2

A tufted carpet with a pile shape of cut pile, a pile length of 10 mm and a pile yarn weight of 1000 g/m² using short staple fibers of 6,6-nylon was dyed with an acidic dye and aqueous solutions containing CAE and fluorine type anti-contaminating agents according to the following recipes were each sprayed on the pile surface of the carpet, followed by drying at 130° C. for 15 minutes.

| Recipe | CAE conc. (wt. %) | Fluorine type anti-contaminating agent (wt. %) |
|---|---|---|
| 1 | 2.5 | 5.0* |
| 2 | 2.5 | 5.0** |
| 3 | 5.0 | 5.0* |

-continued

| Recipe | CAE conc. (wt. %) | Fluorine type anti-contaminating agent (wt. %) |
|---|---|---|
| 4 | 5.0 | 5.0** |

*AG-800 (produced by Asahi Glass Co., Ltd.)
**Teflon C-SF (produced by E.I. Du Pont de Nemours Co.)

A small strip (50 cm × 50 cm) of each carpet was wetted with a small amount of water and kept at a temperature of 37° C. for 10 minutes and thereafter subjected to squeezing. The squeezed fluid was attached in an amount of 50 μl on a paper disc, which was placed on an agar medium containing Bacillus subtilis strain No. AJ-1234 (heart infusion agar medium) and cultivation was conducted at 37° C. overnight. The width of growth inhibition zone formed was measured to give the sterilizing effect of each carpet as shown in Table 2.

TABLE 2

| Recipe | CAE attached (wt. %) | Fluorine type anti-contaminating agent attached (wt. %) | Width of inhibited zone (mm) |
|---|---|---|---|
| 1 | 0.20 | 9.5 | 8.0 |
| 2 | 0.13 | 9.5 | 7.2 |
| 3 | 0.61 | 9.5 | 12.8 |
| 4 | 0.39 | 9.5 | 10.5 |

EXAMPLE 3

A tufted carpet with a pile shape of level loop, a pile length of 5 mm and a pile yarn weight of 1000 g/m$^2$ fabricated with the use of bulky yarns of 6,6-nylon as pile yarns and a polypropylene fabric as foundation was dyed with a cation dye, an acidic dye and a disperse dye and thereafter an antimicrobial agent of an organosilicone quaternary ammonium salt (#5700, produced by Dow Chemical Co.) and CAE were attached on the carpet.

Impregnation treatment with the antimicrobial organosilicone quaternary ammonium salt was performed by dipping the carpet in an aqueous solution of the antimicrobial organosilicone quaternary ammonium salt at 70° C. for 20 minutes and, after dehydration, drying the dipped carpet at 130° C. for 15 minutes. The impregnation treatment with CAE was performed by spraying an aqueous CAE solution, followed by drying at 130° C. for 15 minutes. In the recipes 6 to 8, CAE impregnation treatment was performed after the impregnation treatment with the antimicrobial organosilicone quaternary ammonium salt.

| Recipe | Conc. of antimicrobial organosilicone quaternary ammonium salt (wt. %) | CAE conc. (wt. %) |
|---|---|---|
| 1 | 0 | 0 |
| 2 | 0.017 | 0 |
| 3 | 0 | 0.5 |
| 4 | 0 | 2.5 |
| 5 | 0 | 5.0 |
| 6 | 0.017 | 0.5 |
| 7 | 0.017 | 2.5 |
| 8 | 0.017 | 5.0 |

The amounts of the antimicrobial organosilicone quaternary ammonium and CAE attached onto the pile yarns are shown in Table 3.

TABLE 3

| Recipe | Amount of antimicrobial organosilicone quaternary ammonium salt attached (wt. %) | Amount of CAE attached (wt. %) |
|---|---|---|
| 1 | 0 | 0 |
| 2 | 0.45 | 0 |
| 3 | 0 | 0.1 |
| 4 | 0 | 0.5 |
| 5 | 0 | 1.0 |
| 6 | 0.45 | 0.1 |
| 7 | 0.45 | 0.5 |
| 8 | 0.45 | 1.0 |

The carpet of each recipe obtained was subjected to measurement of the activity for deactivating HBs antigen to obtain the results as shown in Table 4.

The test was conducted according to the method as described in Nippon Iji Shinpo (Medical New Report of Japan) No. 2852. As apparently seen from the results shown in Table 4, the carpets having CAE of the present invention attached thereon are recognized to have the effect of deactivating HBs antigen. In particular, the effect was marked in carpets of the recipes 6 to 8 wherein the antimicrobial organosilicone quaternary ammonium salt was employed in combination.

TABLE 4

| | HBs antigen | | | | | |
|---|---|---|---|---|---|---|
| | High titer (11568 cpm) | | | Low titer (4601 cpm) | | |
| Recipe | cpm | Deactivation (%) | Antigenicity | cpm | Deactivation (%) | Antigenicity |
| 1 | 11747 | 0 | + | 4163 | 2.8 | + |
| 2 | 12086 | 0 | + | 3552 | 17.0 | + |
| 3 | 10265 | 11.3 | + | 2728 | 36.3 | + |
| 4 | 5096 | 55.9 | + | 146 | 96.6 | − |
| 5 | 7052 | 39.0 | + | 95 | 97.8 | − |
| 6 | 5610 | 48.5 | + | 833 | 81.5 | + |
| 7 | 2478 | 78.6 | + | 128 | 97.0 | − |
| 8 | 2666 | 77.0 | + | 0 | 100.0 | − |

Test Method

HBs antigens were prepared using a high titer solution (4096 RIA antibody titer/0.1 ml) and a low titer solution (521 RIA antibody titer/0.1 ml), which were diluted with 0.05 M tris HCl buffer of pH 8.0 (TB buffer) containing 0.5% bovine serum albumin. The quantity of antigen was determined according to radioimmunoassay using $^{125}$I-labelled HBs antibody. That is, to a small strip of a carpet of about 1 cm × 1 cm (0.11 to 0.13 g), there was added 0.1 ml of a HBs antigen solution. The mixture was left to stand at room temperature for one hour, and then 3.1 ml of the TB buffer was added thereto. After incubation for one night, the residual antigen quantity was determined by radioimmonoassay.

We claim:

1. An antimicrobial carpet, comprising an amino acid type surfactant represented by the formula:

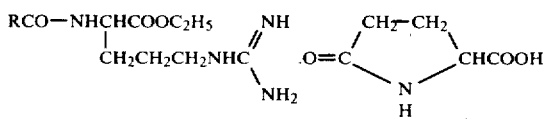

wherein RCO is a $C_8$-$C_{16}$ fatty acid residue, attached on a fibrous material constituting said carpet.

2. A carpet according to claim 1 wherein the content of said amino acid type surfactant is 0.01 to 5% by weight based on the fibrous material.

3. A carpet according to claim 1 wherein a fluorine type anti-contaminating agent is also attached in combination with said amino acid type surfactant.

4. A carpet according to claim 3 wherein the content of a fluorine type anti-contaminating agent is 0.1 to 30% by weight based on the fibrous material.

5. A carpet according to claim 1 wherein an antimicrobial agent of an organosilicone quaternary ammonium salt is also attached in combination with said amino acid type surfactant.

6. A carpet according to claim 1 wherein said antimicrobial agent of an organosilicone quaternary ammonium salt, a fluorine type anti-contaminating agent and said amino acid type surfactant are attached on the fibrous material in combination.

7. A carpet according to claim 5 or claim 6 wherein the ratio of said amino acid type surfactant to said antimicrobial agent of an organosilicone quaternary ammonium salt is 1:5 to 1:0.4 in terms of weight ratio.

8. In a method for preparation of a carpet by fabricating a fibrous material into a carpet, the improvement which comprises subjecting the fibrous material prior to or after fabrication into a carpet structure to a treatment with an amino acid type surfactant represented by the formula:

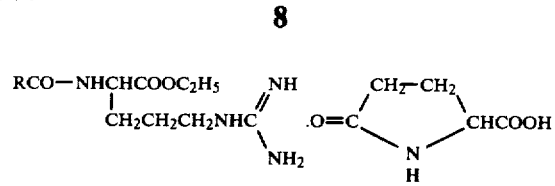

wherein RCO is a $C_8$–$C_{16}$ fatty acid residue, thereby to produce an antimicrobial carpet.

9. A method for preparation of an antimicrobial carpet according to claim 8 wherein the fibrous material is treated with an aqueous solution containing 0.01 to 30% by weight of said amino acid type surfactant thereby to attach onto the fibrous material 0.01 to 5% by weight based on the fibrous material of said amino acid type surfactant.

10. A method for preparation of an antimicrobial carpet according to claim 8 wherein the treatment by impregnation with a fluorine type anti-contaminating agent is applied simultaneously with or after the impregnation treatment with said amino acid type surfactant.

11. A method for preparation of an antimicrobial carpet according to claim 8 wherein the treatment by impregnation with said amino acid type surfactant is performed by use of an antimicrobial agent of an organosilicone quaternary ammonium salt in combination.

* * * * *